United States Patent
Daniel et al.

(10) Patent No.: US 11,684,706 B2
(45) Date of Patent: Jun. 27, 2023

(54) DIALYSIS MACHINE AND CLEANING METHOD FOR THE DIALYSIS MACHINE

(71) Applicant: FRESENIUS MEDICAL CARE DEUTSCHLAND GMBH, Bad Homburg (DE)

(72) Inventors: Pia Daniel, Bodman (DE); Stephan Goessmann, Friedrichsdorf (DE); Klaus Karl, Alzenau (DE); Georg Verch, Wiesbaden (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/462,393

(22) PCT Filed: Nov. 17, 2017

(86) PCT No.: PCT/EP2017/079566
§ 371 (c)(1),
(2) Date: May 20, 2019

(87) PCT Pub. No.: WO2018/091642
PCT Pub. Date: May 24, 2018

(65) Prior Publication Data
US 2019/0336669 A1 Nov. 7, 2019

(30) Foreign Application Priority Data
Nov. 19, 2016 (DE) ...................... 10 2016 013 875.0

(51) Int. Cl.
*A61M 1/16* (2006.01)

(52) U.S. Cl.
CPC .......... *A61M 1/1656* (2013.01); *A61M 1/169* (2013.01); *A61M 1/1688* (2014.02)

(58) Field of Classification Search
CPC .. A61M 1/1656; A61M 1/169; A61M 1/1688; A61M 1/168; A61M 1/1666; A61M 1/3462; A61M 1/3643; A61M 1/3649
See application file for complete search history.

(56) References Cited

U.S. PATENT DOCUMENTS

| | | | | |
|---|---|---|---|---|
| 5,972,223 A * | 10/1999 | Jonsson | ................ | A61L 2/0023 137/88 |
| 2004/0082903 A1* | 4/2004 | Micheli | ................. | A61M 1/284 604/29 |
| 2008/0230450 A1* | 9/2008 | Burbank | ............. | A61M 1/1674 210/92 |
| 2012/0175296 A1* | 7/2012 | Wehmeyer | .......... | A61M 1/1672 210/321.69 |

FOREIGN PATENT DOCUMENTS

| | | |
|---|---|---|
| CN | 103153442 | 6/2013 |
| CN | 103313739 | 9/2013 |
| CN | 1038133816 | 5/2014 |
| CN | 103845768 | 6/2014 |

(Continued)

*Primary Examiner* — Pranav N Patel
(74) *Attorney, Agent, or Firm* — Jacobson Holman PLLC

(57) ABSTRACT

The invention relates to a dialysis treatment unit in which the connecting line to the central concentrate supply is also rinsed in the rinsing or cleaning process in order to prevent deposits therein.

7 Claims, 2 Drawing Sheets

(56) References Cited

FOREIGN PATENT DOCUMENTS

| CN | 105233356 | 1/2016 |
|---|---|---|
| DE | 10256584 | 5/2004 |
| DE | 102011008223 | 7/2012 |
| EP | 0622086 | 11/1994 |
| JP | 2010253130 | 11/2010 |
| WO | WO 2007/148442 | 12/2007 |
| WO | WO 2012/166377 | 12/2012 |

\* cited by examiner

DIALYSIS MACHINE AND CLEANING METHOD FOR THE DIALYSIS MACHINE

TECHNICAL FIELD

The invention relates to a dialysis machine, which requires less maintenance and also relates to a cleaning method for reducing the need for maintenance.

BACKGROUND

In chronic hemodialysis for treatment of renal insufficiency, approximately 120-180 liters of dialysis solution are needed per treatment.

This dialysis solution is usually prepared by the treatment machine on site by diluting and mixing an acidic concentrate and a basic concentrate with dialysis water (permeate).

The basic concentrate consists of pure bicarbonate and is prepared almost exclusively as a dry concentrate.

The acidic concentrate is usually supplied as a mixture of table salt (approximately 75% by weight), an acid, KCl, $CaCl_2$, $MgCl_2$ and glucose. This concentrate is usually supplied as a liquid concentrate in containers such as canisters or bags, which supply an adequate amount of concentrate for one or two treatments, i.e., 5-10 liters of concentrate. These canisters are brought directly to the treatment machine by the nursing personnel. The treatment machine then has a concentrate suction wand, for example, with which the concentrate is removed from the canister.

Dialysis clinics, in which several patients are treated at the same time, often have a central concentrate supply. These central concentrate supplies yield the liquid concentrate from a larger packaging unit, for example (e.g., 300-400 liters) through one or more ring lines to the individual treatment sites where, the treatment machines are then connected to this ring line by means of connecting tubing. Each treatment machine can be connected simultaneously to two different concentrate ring lines by means of separate connections.

These central concentrate supply lines offer the advantage that, first, the heavy canisters need not be brought to the treatment site and, second, the volume of waste is reduced due to the larger containers.

It is advantageous to use individual canisters because that makes it possible to adjust the composition of the dialysis solution to the individual requirements of each individual patient being treated. Thus, different concentrations of electrolytes, different acids or even different concentrations of glucose may be indicated, depending on the patient.

In contrast with that, only a uniform concentrate, which is not necessarily optimized for all patients, can be made available per existing ring line. The number of available ring lines is usually limited to one or two.

If concentrate canisters are frequently used to prepare the dialysis solution and/or multiple concentrate ring lines are connected to the dialysis machine, then the contents of the unused concentrate connecting tubing, which are then unused, are left standing, potentially for a longer period of time, which can lead to the following problem.

The connecting tubing from the treatment machine to the ring line of the central concentrate supply is made of plastic. Water can diffuse through this plastic tubing to a slight extent, so there is an increase in the concentration of the concentrate present in the tubing, in particular when there is a prolonged pause in use. Since the liquid concentrates are salt solutions approaching saturation, there may therefore be a buildup of salt crystals in the tubing. These salt crystals are then rinsed into the machine during the next use of the central concentrate supply and can lead to problems there, which can necessitate an unscheduled service call on the machine.

The object of the present invention consists of supplying a treatment machine for hemodialysis, in which the formation of crystals in the treatment tubing of the treatment machine for the central concentrate supply is prevented.

SUMMARY OF THE INVENTION

According to the teaching of the present invention, this object is achieved by a device according to according to the following description as well as a method according to according to the following description.

In accordance with the present teaching, a dialysis treatment unit having a preparation unit for dialysis solution is disclosed. This preparation unit serves to prepare a ready-to-use dialysis solution from at least one concentrate and one dialysis water (permeate). The concentrate can be supplied through a central concentrate supply. This central concentrate supply prepares liquid concentrate through a line means, for example, a ring line, to several treatment stations having dialysis treatment units. The dialysis treatment unit has a connecting means, which can be connected to the line means of the central concentrate supply. This connecting means is connected to a concentrate line of the preparation unit. At least one valve is provided in this concentrate line, by means of which the transfer of concentrate from the connecting means to the concentrate line of the preparation unit can be controlled by a control unit. This control unit is configured to cause the liquid concentrate to be transferred from the connecting means to the concentrate line during a rinsing process and/or a cleaning operation.

In the connecting means, the concentrate which flows out of the line means of the connecting means and into the dialysis machine is replaced by fresh concentrate from the line means of the central concentrate supply. Since these rinsing and/or cleaning methods are carried out regularly, the liquid concentrate in the connecting means is replaced regularly, independently of the concentrate source used. The increase in concentration of the concentrate and the formation of crystals in the connecting means are therefore prevented.

The transfer of concentrate from the connecting means into the concentrate line can be created by opening the at least one valve in the concentrate line, if there is a higher pressure in the connecting means than in the concentrate line between the at least one valve and the preparation unit. The line means of the central concentrate supply is under an excess pressure as a standard. This excess pressure may amount to 0.05 bar to 2 bar, for example. A reduced pressure of −0.1 bar or less, for example, may exist in the concentrate line between the at least one valve and the preparation unit.

Several valves may also be provided in series connection in the concentrate line, and then may be opened at the same time. When the valves are opened, the pressure is equalized by transferring the concentrate out of the connecting means and into the concentrate line. On opening the valves, the pressure is equalized by transferring the concentrate out of the connecting means and into the concentrate line.

The opening of the valve or valves may take place over a period of 0.5 to 5 s, so that a sufficient amount of concentrate, e.g., 12 mL, is transferred.

The amount of concentrate transferred depends on the length of the connecting means, the difference in pressure, the viscosity of the concentrate and the flexibility of the central concentrate supply, for example. At a pressure of −0.2 bar in the concentrate line of the dialysis machine and with a connecting means 3 meters long, approximately 12 milliliters of concentrate per second are drawn in. the valve opening may thus amount to 1 s, for example.

The valve opening and thus the transfer of the concentrate may preferably take place in an early phase of the rinsing or cleaning method, e.g., the rinsing or cleaning solutions are conveyed into the concentrate line. This ensures that crystals, which enter the concentrate line together with the concentrate, for example, are reliably rinsed out. Furthermore, chemical reactions between the disinfection solution and the concentrate are prevented for the case when dialysis water (permeate), cleaning solutions or disinfection solutions are conveyed into the concentrate line after rinsing solutions, e.g., dialysis water (permeate).

The connecting means may be formed by plastic tubing, e.g., a PVC tubing.

The rinsing or cleaning method may be a disinfection method.

In addition, the invention also relates to a rinsing process for a dialysis treatment unit. This rinsing process serves as a preparation method for the dialysis treatment unit, which is carried out regularly between two days of treatment in order to provide a clean, disinfected dialysis treatment unit for the next treatment. In addition to the rinsing steps with dialysis water (permeate) or cleaning solutions or disinfection solutions, the rinsing process also includes a rinsing step for the connecting means to the central concentrate supply. In the rinsing process for the dialysis treatment unit, comprising a preparation unit for dialysis solution having a concentrate line with at least one valve and having at least one connecting means for connecting the concentrate line to a line means of a central concentrate supply unit, concentrate is first transferred out of the connecting means and into the concentrate line to prevent formation of crystals, and then the rinsing steps are formed are carried out to clean an d disinfect the dialysis treatment unit.

The concentrate can be transferred out of the connecting means and into the concentrate line by supplying a valve in the concentrate line, adjusting a reduced pressure in the concentrate line between this valve and the preparation unit and opening this valve for a predetermined period of time. Following the equalization of pressure, then a certain volume segment of liquid concentrate is transferred out of the connecting means and into the concentrate line. After closing the valve, the liquid concentrate that has flowed out of the connecting means is replaced by fresh concentrate from the central concentrate supply unit, which has the correct composition. The increase in concentration of the concentrate in the connecting means to the central concentrate supply is prevented. The reduced pressure set in the concentrate line may amount to −0.1 bar or less. The valve opening may take place for 0.5 to 5 s. The rinsing process may be a method for disinfection of the dialysis treatment unit.

DETAILED DESCRIPTION OF ONE EXEMPLARY EMBODIMENT

Figure 1:
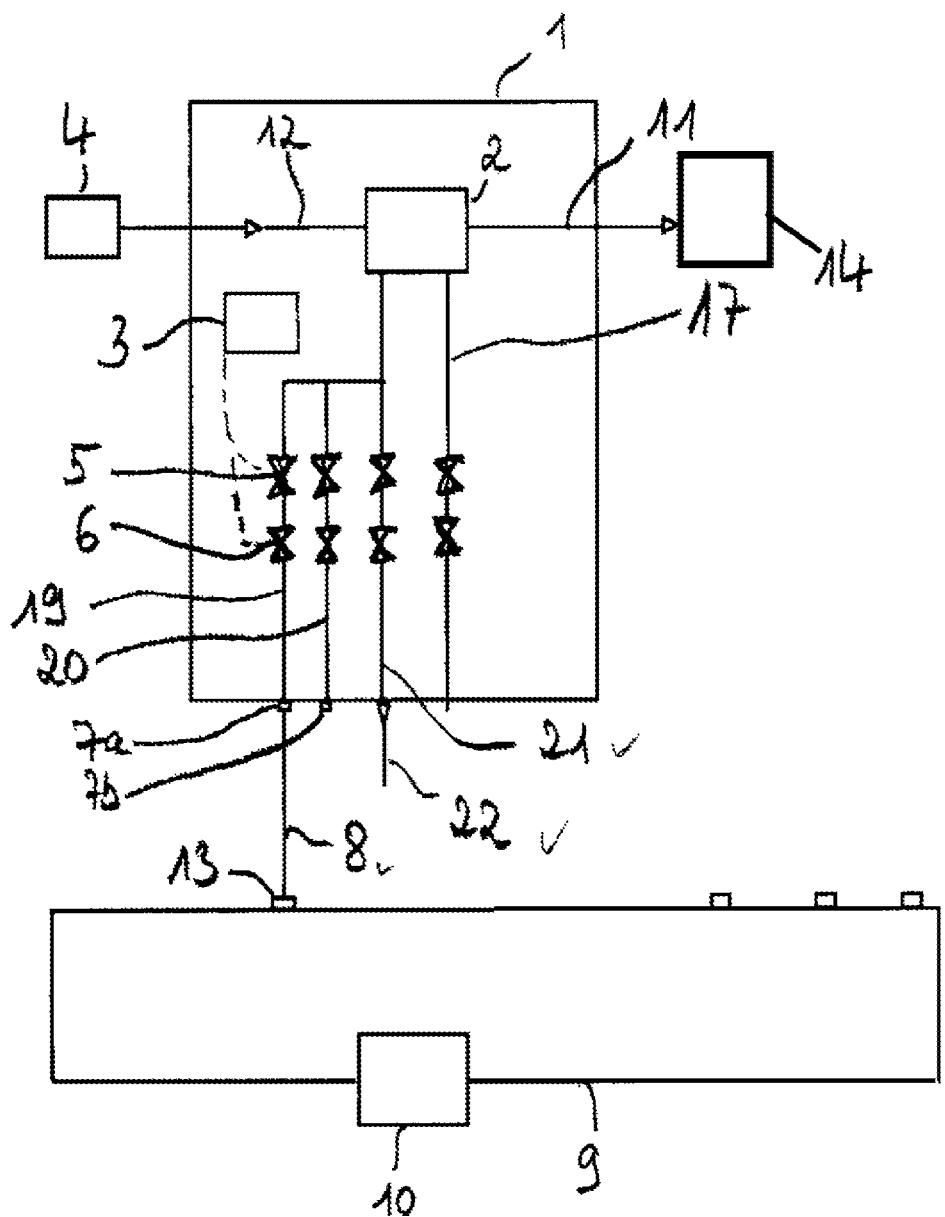
FIG. 1 shows schematically the design of a dialysis treatment unit.
Figure 2:
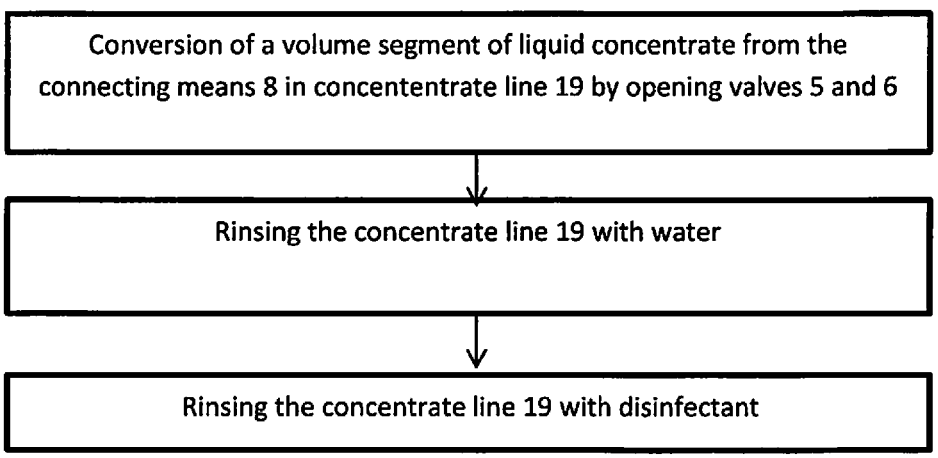
FIG. 2 shows schematically the flow chart of the method.

Dialysis treatment unit 1 prepares dialysis solution online from dialysis water (permeate) and concentrate by means of a preparation unit 2. The dialysis water (permeate) is supplied to the preparation unit 2 from a reverse osmosis system 4 through the line 12. The dialysis solution is usually prepared by diluting and mixing an acidic concentrate and a basic concentrate with dialysis water (permeate). A concentrate line 17 is provided for the basic concentrate. However, it is also possible that a connection to a central concentrate supply unit (not shown) for the basic concentrate is provided. The ready-to-use dialysis solution is then supplied to a treatment module 14, from which the dialysis solution is then transferred further to a dialysis filter (not shown), for example, through the line 11.

In modern dialysis treatment units, several options can be selected for the acidic concentrate in most cases. For example, the acidic concentrate can be removed from the canister with a concentrate suction wand 22 and transported to the preparation unit 2 through a concentrate line 21. However, the acidic concentrate can also be supplied from a central concentrate supply 10. The dialysis treatment unit 1 has connectors 7a and 7b for the connection to a central concentrate supply 10. One end of a connecting means 8, for example, a plastic tubing, may be connected to the connector 7a. The second end of the connecting means 8 is connected to a connector 13 of the ring line 9 of the central concentrate supply 10. Whereas a fluid exchange is always taking place in the ring line 9, the passage in the connecting means 8 exists only when concentrate is being obtained only from the central concentrate supply 10. The dialysis treatment unit 1 has a control unit 3, which is configured to open the valves 5 and 6 during a cleaning method. Since an excess pressure of 0.5 to 2.0 bar prevails as the standard in the ring line 9 of a central concentrate supply unit 10 and a reduced pressure of −0.2 bar prevails behind the valves 5 and 6 in the concentrate line 19, a certain fluid volume is conveyed into the concentrate line 19 with the opening of the valves 5 and 6. Concentrate line 20, like concentrate line 19, can be used for delivering a second concentrate into the dialyses treatment unit. Thus, with a valve opening for one second, approximately 12 mL concentrate is conveyed. Since the cleaning method is used regularly, i.e., whenever the dialysis treatment unit 1 is used, there is a regular exchange of concentrate in the connecting means 8. This prevents the formation of deposits in the connecting means 8. Additional solutions used in the rinsing process, such as disinfectants, can also be sent to the preparation unit 2 and distributed from there (not shown).

In contrast with the known rinsing processes, the rinsing process has an additional process step, namely the transfer of a volume segment of liquid concentrate out of the connecting means 8 and into the concentrate line 19. The connecting means 8 is then supplied with fresh liquid concentrate through the ring line 9 of the central concentrate supply. Then in the dialysis treatment unit, the liquid-carrying lines of the dialysis treatment unit are rinsed with dialysis water (permeate) to rinse it clear of the concentrate. Following that, the lines are then rinsed with cleaning solution or disinfectant solution and the other steps are carried out to clean the machine. The intermediate rinsing step prevents chemical reactions of the liquid concentrate with cleaning solution or disinfectant solution, for example.

The invention claimed is:
1. A dialysis treatment unit having
a preparation unit for dialysis solution preparation,
an acid concentrate line connected independently to the preparation unit,
a base concentrate line connected independently to the preparation unit, a water line connected independently to the preparation unit, at least one plastic tubing having first and second opposing ends, the first opposing end connected to the acid concentrate line and the second opposing end capable of being connected to a ring line of a central acid concentrate supply system, at least one valve in the acid concentrate line, and a control unit controlling opening of the at least one valve and configured to cause the transfer of acid concentrate out of the at least one plastic tubing and into the acid concentrate line during a rinsing or cleaning process in order to prevent crystal binding in the at least one plastic tubing.

2. The dialysis treatment unit according to claim 1, wherein a reduced pressure prevails in the acid concentrate line between the at least one valve and the preparation unit and the transfer of the acid concentrate takes place by simply opening the at least one valve.

3. The dialysis treatment unit according to claim 2, wherein the reduced pressure in the acid concentrate line between the at least one valve and the preparation unit amounts to −0.1 bar or less.

4. The dialysis treatment unit according to claim 2, wherein in the at least one plastic tubing there is an excess pressure of 0.05 to 2 bar.

5. The dialysis treatment unit according to claim 2, wherein the control unit opens the at least one valve for a period of 0.5-5 s.

6. The dialysis treatment unit according to claim 1, wherein the control unit opens the at least one valve before rinsing or cleaning solutions are delivered into the acid concentrate line in the rinsing or cleaning process.

7. The dialysis treatment unit according to claim 1, wherein the rinsing or cleaning process is a disinfection process.

* * * * *